United States Patent [19]
Buckner

[11] 3,938,508
[45] Feb. 17, 1976

[54] ORAL APPLIANCE FOR BURN PATIENTS

[76] Inventor: Horst E. Buckner, R.R. No. 1, Iowa City, Iowa 52240

[22] Filed: July 26, 1974

[21] Appl. No.: 492,147

[52] U.S. Cl............... 128/76 R; 128/12; 128/136
[51] Int. Cl.² ......................................... A61F 5/08
[58] Field of Search............... 128/76, 136, 12–20; 32/33–35, 40

[56] References Cited
UNITED STATES PATENTS

| | | | |
|---|---|---|---|
| 1,813,650 | 7/1931 | Whitlock | 32/35 |
| 2,061,936 | 11/1936 | Engelfried | 128/12 |
| 2,568,317 | 9/1951 | Bump | 32/35 |
| 2,708,931 | 5/1955 | Freedland | 128/136 |
| 2,850,008 | 9/1958 | Resch | 128/20 |
| 3,454,001 | 7/1969 | Stockfisch | 128/76 R |
| 3,735,491 | 5/1973 | Pabalan, Jr. | 32/33 |

FOREIGN PATENTS OR APPLICATIONS
276,257  8/1927  United Kingdom................ 128/12

Primary Examiner—Richard A. Gaudet
Assistant Examiner—J. Yasko
Attorney, Agent, or Firm—James C. Nemmers; Haven E. Simmons

[57] ABSTRACT

An oral appliance for persons who have suffered facial burns to prevent shrinkage of the tissues around the mouth and lips during the healing process (microstomia). The appliance is adjustable to fit the patient's mouth and can be enlarged to progressively widen the opening of the mouth if shrinkage has already occurred. It may be employed to prevent shrinkage of the mouth and the lips by other causes (scleroderma, etc.).

8 Claims, 2 Drawing Figures

ORAL APPLIANCE FOR BURN PATIENTS

BACKGROUND OF THE INVENTION

Each year thousands of persons suffer burns as the result of accidents. Unfortunately, many of these individuals suffer extensive facial burns which result in scarring. During the healing process, the tissues around the mouth and the lips shrink. This shrinkage can permanently reduce the size of the mouth opening resulting in problems in eating, dental care, and speech as well as appearance. Presently, correction of microstomia requires surgical treatment. But the result may be functionally and cosmetically less than perfect, and the microstomia may recur. It is known that scars from burns can be remodelled by pressure. However, there is no known technique for retarding or preventing shrinkage of the tissues around the mouth and the lips. Because of the number of burn patients who suffer this deformity, there is a need for any technique or device which can help these persons, particularly if the technique or device is simple and inexpensive.

SUMMARY OF THE INVENTION

The invention employs a technique and device which will maintain the size of the opening of the mouth during the healing process in a simple painless manner. The device constructed according to the principles of the invention is preferably made in two different sizes, each of which is adjustable to fit the patient. Because of its adjustability, the device can also be used to progressively widen the oral opening if shrinkage has already occurred. The device of the invention is very simple consisting of two end members contoured to fit the lips at the sides of the opening of the mouth, the end members being connected by two bars which are movable to each other and which can be maintained in a desired relative position thus providing for adjustment of the distance between the two end members. The device is very simple and inexpensive to manufacture and is very simple to use so that the patient himself can use the device without assistance.

DESCRIPTION OF THE PREFERRED EMBODIMENT OF THE INVENTION

Figure 1:
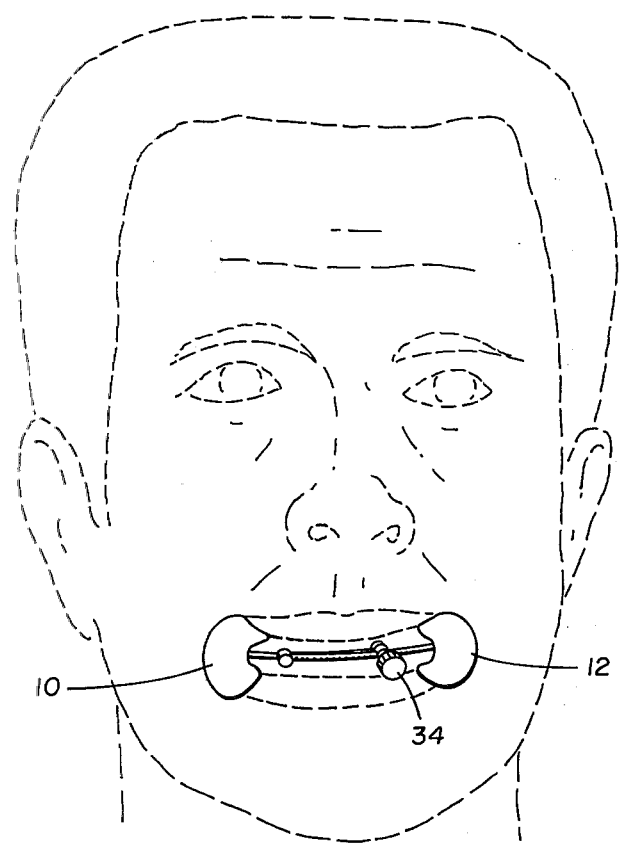
FIG. 1 is a front view showing the device in place in the mouth.
Figure 2:
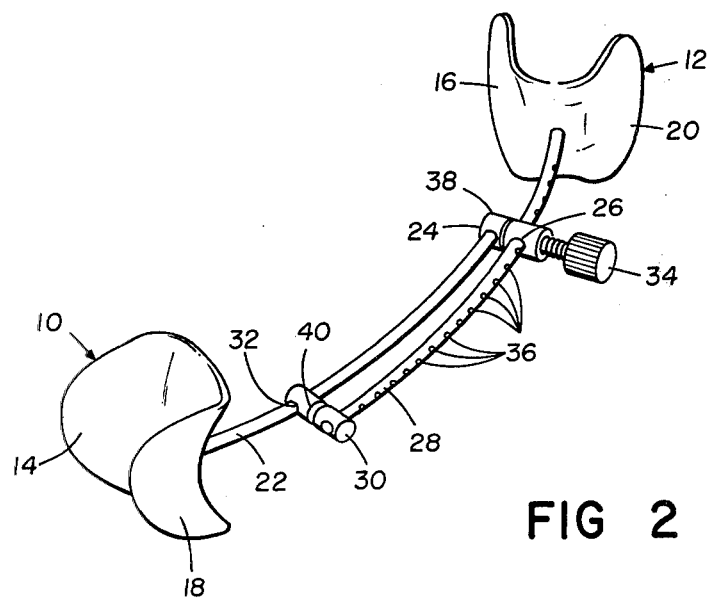
FIG. 2 is a perspective view of the device removed from the mouth.

In FIG. 1 of the drawing, there is shown a frontal view of a patient with an oral appliance constructed according to the principles of the invention shown in place in the mouth of the patient. As previously indicated, one of the primary uses for the invention is to prevent shrinkage of the mouth opening during the healing process where extensive facial burns have occurred. The lips and the tissues around the mouth are normally capable of being stretched when the mouth is opened to speak, eat, etc. However, because of the scarring left by facial burns the tissues are damaged and when the healing process is complete the tissues cannot be stretched to permit normal speech or eating. In other words, the size of the mouth opening will permanently shrink. The device of the invention is designed to slightly stretch the mouth opening and maintain it in that position during the healing process thus eliminating the shrinkage. The device, therefore, consists of two end members 10 and 12 each of which is contoured to fit the lips at the sides of the mouth. The end members 10 and 12 therefore have outwardly extending wings 14 and 16 which fit inside of the mouth and outwardly extending exterior wings 18 and 20 respectively which fit along the lips outside of the mouth. Preferably, the inside wings 14 and 16 are larger than the exterior wings 18 and 20 so as to better maintain the device in place. The end members 10 and 12 have rounded smooth edges and no corners and are contoured so as to comfortably fit along the lips at the sides of the mouth. The end members 10 and 12 therefore are preferably molded of plastic or other suitable material, which allows additions to the end members.

End member 10 has rigidly affixed to it a convexly curved bar 22 which has affixed to it at its opposite end an abutment member 24 that extends forwardly and substantially transversely to the curved bar 22. Abutment member 24 has an opening 26 extending transversely through it near its forward end which opening extends in a direction somewhat parallel to the bar 22. The opening 26 has slidably received therein a second curved bar 28 which has one end rigidly affixed to end member 12 and has at its opposite end an abutment member 30 which extends rearwardly and substantially transversely to the curved bar 28. Abutment member 30 has an opening 32 extending transversely near its rearward end which opening slidably receives the curved bar 22. Thus, although each of the curved bars 22 and 28 are rigidly affixed to the end members, and end members 10 and 12 are movable generally toward and away from each other as the curved bars 22 and 28 slide respectively in the openings 26 and 32 in the abutment members 24 and 30.

The curved bars 22 and 28 are preferably of the same length. Thus, the end members can be moved to an infinite number of relative positions between the closest position of approximately the length of one of the curved bars 22 or 28 to the farthest position of approximately the combined length of the curved bars 22 and 28. Since the abutment members 24 and 30 are affixed to the ends of the curved bars 22 and 28 respectively, the abutment members will limit the distance to which the end members can be moved since the abutment members will serve as stops when they engage the end members 10 and 12 as the end members are moved closest to each other, and the abutment members 24 and 30 will engage each other when the end members are moved to the farthest extended position.

The relative movement between the end members 10 and 12 that is provided by the foregoing described construction provides for adjustment of the distance between the two end members 10 and 12 so that the appliance of the invention will fit the mouth of the patient. In order to maintain the relative position of the end members 10 and 12 in a preselected position to fit the mouth of a particular patient, I prefer to provide a set screw 34 that is threaded into the forward end of the abutment member 24 so that the set screw 34 will engage that portion of the curved bar 28 that extends through the opening 26. If desired, a series of indentations 36 can be provided in the forward end of the curved bar 28 each of which indentations 36 will provide a seat for the end of the set screw 34 when it is tightened thereby providing a positive lock to position the end members 10 and 12.

If desired, the abutment members 24 and 30 may each be provided with circumferential grooves 38 and 40, respectively. An elastic member (not shown) can then be placed in the grooves 38 and 40, and after removal of the set screw 34, the elastic member fitted in grooves 38 and 40 will contract and force the end members 10 and 12 apart. This will apply constant pressure through the end members 10 and 12 to the two corners of the mouth thus providing for continuous expansion and constant outward pressure mouth opening. An appliance, modified in this manner, can be used for the training of certain facial muscles. The facial muscles are trained and strengthened by working against the pressure of the elastic.

From the foregoing description it will be evident to those skilled in the art that use of the device of the invention provides a technique that enables correction and prevention of a serious deformity resulting from facial burns. If the appliance of the invention is used during the healing process, it can almost entirely eliminate shrinkage of the tissues that causes contraction of the opening of the mouth. The appliance also can be used for post-traumatic therapy in order to widen the opening of the mouth where shrinkage has already occurred. In this regard, the adjustability of the relative position of the end members 10 and 12 provides for progressive widening of the opening of the mouth with a minimum of pain and trauma to the patient. The appliance of the invention and the technique of its use represent a significant advance in the art, and although only the preferred embodiment of the appliance has been disclosed herein, it will be obvious to those skilled in the art that the technique of the invention can be employed using appliances different from that of the preferred embodiment. It is my intention, however, that all modifications and variations to the preferred embodiment disclosed herein are within the spirit and scope of the invention. It is, therefore, my intention that all such variations and modifications which are obvious to those skilled in the art will be included within the scope of the following claims.

I claim:

1. An oral appliance for treating patients with facial burns, said appliance comprising a pair of spaced-apart end members each having an outer wing and an inner wing joined together along a edge to form a concave-shaped end member with the wings extending outwardly away from the outwardly extending wings of the other end member, said end member being of a size to engage and fit the patient's lips only at opposite corners at the sides of the opening of the patient's mouth, and adjustable means connected to said end members at a place centrally of each of them and providing for adjustable relative movement between said end members to vary the distance between them, said adjustable means terminating at the place of connection to each said end member and lying entirely between said end members regardless of the relative position of said end members.

2. The oral appliance of claim 1 in which said means connected to said end members includes means for maintaining a preselected relative position of said end members.

3. The oral appliance of claim 1 in which said means connected to said end members includes means biasing said end members away from each other.

4. An oral appliance comprising a pair of spaced-apart end members each shaped to fit the lips at opposite corners of the opening of the mouth, means interconnecting said end members and providing for adjustable relative movement between said members, said means including a first bar affixed to the first one of said end members and extending toward the other end member, a second bar affixed to the other of said end members and extending toward the first one of said end members, and an abutment member on the outer end of each of said first and second bars, each of said abutment members having an opening therein through which the bar connected to the other abutment member slidably extends.

5. The oral appliance of claim 4 in which one of said abutment members has a set screw threadedly received therein, the end of said set screw extending through the abutment member into the opening therein where it is engageable with one of said bars slidably received in said opening, tightening of said set screw thereby holding the bar it engages in a fixed position in said abutment member so as to fix the relative position of said end members.

6. The oral appliance of claim 5 in which said bars are slightly curved convexly so as to fit the natural curvature of the mouth when the appliance is in place in the opening of the mouth.

7. The oral appliance of claim 6 in which each of said end members has a pair of outwardly extending spaced-apart wings, the inner wing being adapted to fit inside of the mouth and the exterior wing being adapted to fit outside of the mouth.

8. The oral appliance of claim 7 in which the inner wing of each of said end members has a larger surface of contact with the inside of the mouth then the exterior wing has with the outside of the mouth.

* * * * *